(12) United States Patent
Feldman

(10) Patent No.: US 7,574,025 B2
(45) Date of Patent: Aug. 11, 2009

(54) ORAL IMPLANT TEMPLATE

(75) Inventor: Andrei Feldman, Haifa (IL)

(73) Assignee: I-Dent Imaging, Inc., Fort Lauderdale, FL (US)

( * ) Notice: Subject to any disclaimer, the term of this patent is extended or adjusted under 35 U.S.C. 154(b) by 660 days.

(21) Appl. No.: 10/501,559

(22) PCT Filed: Jan. 16, 2003

(86) PCT No.: PCT/IL03/00043

§ 371 (c)(1), (2), (4) Date: Jul. 16, 2004

(87) PCT Pub. No.: WO03/060825

PCT Pub. Date: Jul. 24, 2003

(65) Prior Publication Data

US 2005/0084144 A1    Apr. 21, 2005

Related U.S. Application Data

(60) Provisional application No. 60/348,382, filed on Jan. 16, 2002.

(51) Int. Cl.
  G06K 9/00    (2006.01)
  G06K 9/40    (2006.01)
  A61C 3/00    (2006.01)

(52) U.S. Cl. .................... 382/128; 382/275; 433/75

(58) Field of Classification Search .............. 382/128, 382/275; 433/75, 172
See application file for complete search history.

(56) References Cited

U.S. PATENT DOCUMENTS

| 5,725,376 | A | * | 3/1998 | Poirier ................... 433/172 |
| 5,743,916 | A |   | 4/1998 | Greenberg et al. |
| 5,800,168 | A | * | 9/1998 | Cascione et al. ........... 433/75 |
| 5,888,034 | A |   | 3/1999 | Greenberg |
| 5,927,982 | A | * | 7/1999 | Kruger .................... 433/215 |
| 6,118,845 | A | * | 9/2000 | Simon et al. .............. 378/62 |
| 6,201,880 | B1| * | 3/2001 | Elbaum et al. ............ 382/100 |

(Continued)

FOREIGN PATENT DOCUMENTS

DE    100 29 256 A    11/2000

(Continued)

OTHER PUBLICATIONS

R.Jacobs, et al;"Predictability of a Three-Dimensional Planning System for Oral Implant Surgery";Dentomaxillofacial Radiology(1999) 28; pp. 105-111.

(Continued)

*Primary Examiner*—Bhavesh M Mehta
*Assistant Examiner*—John B Strege
(74) *Attorney, Agent, or Firm*—Cohen Pontani Lieberman & Pavane LLP

(57) ABSTRACT

A method for producing an artifact-corrected image of a negative jaw impression in a recipient jaw comprising, forming a negative impression of said recipient jaw, producing a first digital image of said negative jaw impression, producing a second digital image, including said artifacts of said negative jaw impression in said recipient jaw and using said first digital image to produce an artifact-corrected computer representation of said negative impression in said recipient jaw.

11 Claims, 5 Drawing Sheets

U.S. PATENT DOCUMENTS 6,488,503 B1 * 12/2002 Lichkus et al. .......... 433/202.1
6,859,565 B2 * 2/2005 Baron ..................... 382/275
2004/0078212 A1 4/2004 Andersson et al.

FOREIGN PATENT DOCUMENTS

EP 0 544 505 A 6/1993
FR 2 700 039 A 7/1994

OTHER PUBLICATIONS

Van Steenberghe et al;"A Custom Template & Definitive Prosthesis . . . "; (Int J Oral Maxillofac Implants;2002; 17:663-670).

* cited by examiner

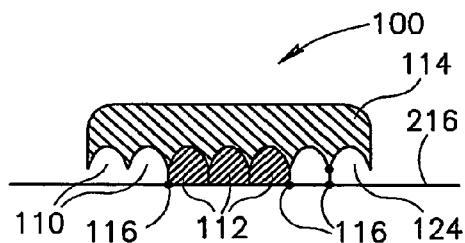
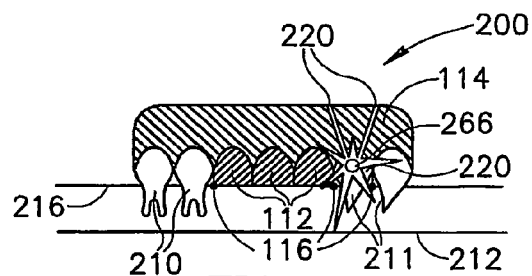
FIG.1  FIG.2
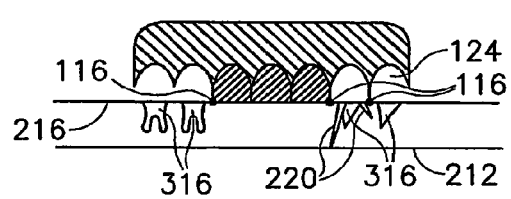
FIG.3
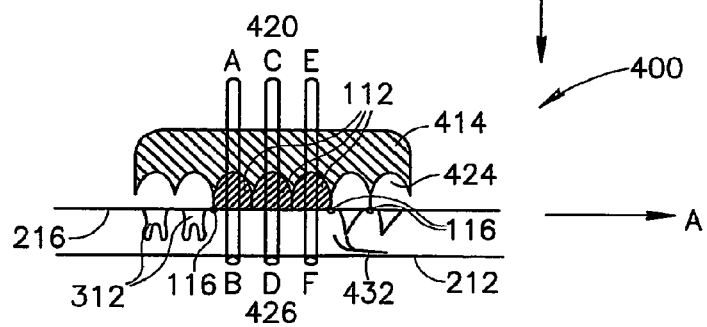
FIG.4
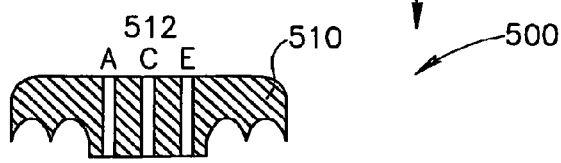
FIG.5

A →

B →

ORAL IMPLANT TEMPLATE

RELATED APPLICATION

This application claims benefit under 119(e) of U.S. provisional patent application 60/348,382, filed Jan. 16, 2002, the disclosure of which is incorporated herein by reference.

FIELD OF THE INVENTION

The present invention relates to creating an oral implant drilling template.

BACKGROUND OF TIE INVENTION

A drilling template is a negative blank of a recipient jaw with at least one drilling guide for positioning one or more tooth implant bores in the recipient jaw. An aesthetically pleasing implanted tooth is dependent upon proper bore placement and depth in relation to other teeth, placement in appropriate jaw bone stock and duplication of the angle of adjacent teeth in the recipient jaw, all of which must be incorporated into the drilling template. For the purposes of this application, the words "recipient jaw" refers to the teeth, gums, landmarks, supportive and ancillary structures within the area that is designated to receive an implant.

In one method for creating a drilling template known in the art, such as in Poirier, U.S. Pat. No. 5,725,376, coordinates of radio opaque markings along with a jaw image, taken with CT or MRI, are used by a CNC machine to drill holes in a negative impression of the recipient jaw. The resultant drilling template is used in drilling bores for implants in the recipient jaw. Use of a CNC machine, though, is undesirable in a clinic setting.

For the purposes of this application, "drilling template" and "negative impression" refer to physical objects utilized in the production of drilling implant bore guides. For the purposes of this application, a "model" is further defined as a physical object, such as a model of a jaw, created from a computer representation.

In a second method for creating a drilling template that, for the purpose of this application is referred to as the "boundary method", boundary information is taken from a digital image of the recipient jaw, such as from a CT or MRI image. This digital boundary information is entered into an image processing unit and used to form a computer representation of a negative mouth impression. Drill holes are subtracted from the computer representation and the resultant data is sent to a machining process, such as a CNC Machine, to create a drilling template.

For the purposes of this application, an "image" or "digital image" refers to an image taken, for example, by a CT or MRI imaging unit that is transferred digitally to a digital processing unit.

For the purposes of this application, a "computer representation" refers to a digital image that has been processed by a digital processing unit, for example, to place drill bores within the computer representation.

A proper implant drilling template, created utilizing the boundary method, begins with creating a proper image, using CT for example, of the recipient jaw. When the recipient mouth contains metal inserts such as tooth fillings, the image produced using CT contains many artifacts that smear and/or distort the true surface boundaries of the recipient jaw. Since image artifacts are improperly removed to recreate the surface boundaries, the drilling template used to guide the drilling of tooth implant bores often provides an aesthetically displeasing implanted tooth or an unusable drilling template.

Prior art image correction software, unfortunately, relies on default settings to reconstruct the jaw image hidden by artifact distortion, a process wherein the software estimates the distorted jaw boundaries. A drilling template that is made according to this estimated jaw model may not be supported by adjacent teeth and/or may have improperly aligned drilling guides. The resultant tooth implant will be out of line with adjacent teeth or, worse, implanted into a non-supportive bone section in the recipient jaw bone.

Another problem in constructing a pleasing implanted tooth using the boundary method, occurs in properly mounting the finished drilling template on the recipient jaw area. When the teeth adjacent to the planned implants have complex concavity and/or convexity, the resultant drilling template often is difficult to mount or remove from the jaw. In the presence of such curvature complexity, imaging software will often rely on default settings to smooth out such curvatures, again yielding a drilling template with improper drilling guides and resultant aesthetically displeasing implanted teeth.

Kruger, U.S. Pat. No. 5,927,982, attempts to create a drilling template from a negative mouth impression modified using a CT scan of the recipient jaw area. The correct bore placement is identified in the CT scan and, using a multi-axis drilling platform, the negative impression is drilled. This method of drilling a negative impression is cumbersome and, worse, imprecise. As Kruger notes, the CT scan is adversely affected by "metal restorations or prostheses that will cause scatter" (column 7 line 34). This results in image aberrations that his method cannot correct, yielding a drilling template from which misaligned implant bores are drilled or an unusable drilling template.

Swaelens et al., WO 95/28688 provides an imaging method for determining muscle and tendon position that may be helpful in determining tooth implant bore location, but fails to teach how to correct surface boundaries distorted by metal inserts or correct for complicated tooth curvatures. As a result, the resultant drilling template may provide inaccurate bore placement and aesthetically displeasing results.

SUMMARY OF THE INVENTION

An aspect of some embodiments of the present invention relates to methods for creating an oral implant drilling template from an artifact-corrected computer representation of the recipient jaw.

In an exemplary embodiment of the present invention, a negative impression is made of a recipient jaw and two digital images are made using, for example, CT, MRI or another imaging system. A first distorted image is made that includes the negative mouth impression installed in the recipient jaw including the metal inserts, for example metal fillings, and their resultant artifacts. A second image is made only of the negative impression. As the negative impression template does not include metal inserts, the resultant image correctly reproduces an image that is free of artifacts.

The second image of the negative impression is used to digitally reconstruct the boundary in the first distorted image of the negative impression installed in the recipient jaw. The computer representation derived from the combination of the two images is corrected of artifacts that adversely affect the modeling process leading to formation of a proper drilling template.

In an embodiment of the present invention, an artifact-corrected computer representation of the recipient jaw and negative impression template is used to create a drilling template without intermediary modeling steps. The artifact-corrected computer representation is manipulated to include drill bore images. Optionally, a modeling process, such as a Fast Prototyping machine is used to create a finished, properly aligned, drilling template from this manipulated computer representation.

In an embodiment of the present invention, an artifact-corrected computer representation that has been manipulated to include drill bore images, is used to create a drilling template following intermediary modeling steps. Optionally, the artifact-corrected computer representation is used to create a model of the jaw area, including drill bores, using, for example, a modeling process, for example a Fast Prototyping machine. Optionally, the bored jaw model is then used to bore drilling guides into the NIT, forming the NIT into a suitable drilling guide that is optionally used to drill implant bores in the recipient jaw.

In an embodiment of the present invention, when the negative impression contains complex curvatures, the resultant drilling template, made from combined first and second images of the NIT, is often difficult to insert and remove from the recipient jaw. Optionally, when the negative mouth impression contains complex curvatures, prior to imaging the negative impression and correcting for artifacts, the NIT is smoothed, to allow easy insertion and removal from the recipient jaw. Optionally, the smoothing process uses, for example, machinery known in the art, for example, dental modeling machinery.

In an exemplary embodiment of the present invention, prior to drilling bores in the recipient jaw, the drilling template is tested to ensure that it sits properly in the jaw so that the drilled bores will be properly aligned. In an embodiment of the present inventions, the resultant drilling template is imaged in the recipient jaw, using an imaging process, for example X-ray, CT or MRI, to ensure that it seats properly. The image is then analyzed by image analyzing software or by manual inspection by the operator. When the analyzed image indicates probable difficulties in seating in the recipient jaw, the drilling template is optionally modified using, for example, dental modeling machinery so that it seats properly in the recipient jaw.

Additionally or alternatively, the drilling template is returned to a modeling process, for example a Fast Prototyping machine, for modification according to the imaging analysis. Following modification, the drilling template is optionally imaged to ensure that it seats properly in the recipient jaw. Provided no further modifications are required, the drilling template is used as a drill guide to drill bores in the recipient jaw to receive tooth implants.

An aspect of some embodiments of the present invention relates to an alternative method for creating a properly aligned drilling template where there are no metal inserts causing artifacts. A digital image of the recipient jaw is manipulated to create a computer representation of the recipient jaw with one or more bores for tooth implants. Optionally, a modeling process, for example a Fast Prototyping machine is used to create a model of the recipient jaw including the bores. A negative impression of the jaw is fixed on the jaw model and the drilling guides of the jaw model are continued through the negative impression to create a properly aligned drilling template.

Optionally, the digital image of the jaw is used to create a drilling template without creating a jaw model. In an embodiment of the invention, a modeling process, for example a Fast Prototyping machine, is used to directly create a drilling template with properly aligned bores. Optionally, as in prior embodiments, the resultant drilling template is imaged and modified to ensure that it seats properly in the recipient jaw, prior to drilling tooth implant bores in the recipient jaw.

There is thus provided in accordance with an exemplary embodiment of the present invention, a method for producing an artifact-corrected image of a negative jaw impression in a recipient jaw comprising forming a negative impression of said recipient jaw, producing a first digital image of said negative jaw impression, producing a second digital image, including said artifacts, of said negative jaw impression in said recipient jaw and using said first digital image to produce an artifact-corrected computer representation of said negative impression in said recipient jaw.

Optionally, said negative jaw impression is adjusted during formation to allow easy manipulation of said impression on said recipient jaw. Optionally one or more tooth implant models are set in said negative jaw impression prior to producing said images.

Optionally, one or more reference markings are incorporated in said negative jaw impression wherein said reference markings are visible in said first and second images. Optionally, said reference markings comprise one of the following: points, edges, planar edges or lines.

In an embodiment of the present invention said first and second digital images comprise voxels. Optionally, the voxels of said first digital image are aligned with the voxels of said second digital image. Optionally, aligning the voxels of said first digital image with the voxels of said second digital image uses one or more of said reference markings in said first and second images. Optionally, aligning the voxels of said first digital image with the voxels of said second digital image uses the boundaries of said images. Optionally, alignment software is used to align said first digital image with said second digital image. Optionally, the voxels of said first digital image are substituted for said aligned voxels of said second digital image. Optionally, the formed image comprises the upper portion of the first image and the lower portion of the second image wherein said upper portion is free of said artifacts.

In an embodiment of the present invention, one or more drilling trajectories are set in said artifact-corrected computer representation. Optionally, said artifact-corrected computer representation is used to produce a drilling template. Optionally one or more drill bore guides are included in said drilling template.

In an embodiment of the present invention, said artifact-corrected computer representation is used to produce a model of said recipient jaw. Optionally, one or more drill bores are placed in said recipient jaw model. Optionally, said model of said recipient jaw is used to produce a drilling template. Optionally, said negative impression of said recipient jaw is used to produce said drilling template. Optionally, one or more drill bore guides are placed into said drilling template.

There is thus provided, in accordance with exemplary embodiments of the present invention, a method for producing a model of a recipient jaw from which a drilling template is machined, comprising producing a 3D digital image of said recipient jaw, placing bore trajectories in said 3D digital image and producing a model of said recipient jaw from said 3D digital image.

In an exemplary embodiment, said 3D digital image is enhanced to allow easy manipulation within said recipient jaw. Optionally, said recipient jaw model is used to produce a negative template of said model.

In an exemplary embodiment, boring trajectories are produced within said negative template of said model. Optionally, said model of said recipient jaw contains representations of one or more of the following structures: nerves, bone, teeth, cartilage and soft tissue. In an exemplary embodiment, said jaw model is used to produce boring trajectories within said negative template of said model.

In an embodiment of the present invention, a drilling template is placed in said recipient jaw and an image is made to determine that it seats properly. Optionally, the image is used to determine that the planned trajectories are properly aligned. Optionally, an image of said drilling template is placed on a model of said recipient jaw and analyzed to determine that said drilling template seats properly.

In an embodiment of the present invention, said drill drilling template is placed in said recipient jaw and said drilling template is used to drill implant receiving bores in said recipient jaw.

According to an aspect of some exemplary embodiments of the present invention, there is also provided an apparatus having a first input adapted to receive a digital image of a recipient jaw including artifacts and a second input adapted to receive a digital image of a negative impression of said jaw. Said apparatus further comprises a digital merging unit adapted to receive and merge said first and second digital inputs to form a reproduced image having reduced artifacts with reference to said first image.

In an exemplary embodiment, said digital merging system further comprises a negative jaw impression adjuster adapted for adjusting said impression to allow easy manipulation of said impression on said recipient jaw. Optionally, the system comprises a tooth implant model setter that sets one or more tooth implant models in said negative jaw impression, prior to producing said images.

In an exemplary embodiment, the digital merging system includes a reference marking recorder that places reference markings in said negative jaw impression. Optionally, said merging of said first and second images utilizes said one or more markings during said merging.

In an exemplary embodiment, the images are voxel images. Alternatively or additionally, the digital merging system includes alignment software having a voxel alignment module that aligns the voxels of said first digital image with the voxels of said second digital image.

Alternatively or additionally, the software includes a voxel substituting module that substitutes at least a portion of said first digital image for voxels of said second digital image.

In an exemplary embodiment, the digital merging system comprises an image conglomerator software module that conglomerates a portion of the first image with a portion of the second image, wherein the images are non-inclusive. In an exemplary embodiment, the conglomerator conglomerates the upper portion of the first image and the lower portion of the second image. Optionally the software comprises a drill trajectory imposer module that imposes one or more drilling trajectories in said artifact-reduced image.

In an exemplary embodiment, the digital merging system includes a drilling template modeler that receives said reproduced image and models a drilling template based upon said image. Optionally, the drilling template modeler comprises a fast prototyping machine. Alternatively or additionally, the drilling template modeler comprises a negative impression modifier that modifies a negative impression to produce a drilling template. In an exemplary embodiment, the negative impression modifier comprises a drilling machine that drills said negative impression to produce said drilling template.

BRIEF DESCRIPTION OF THE DRAWINGS

Exemplary non-limiting embodiments of the invention will be described with reference to the following description of embodiments in conjunction with the figures. Identical structures, elements or parts which appear in more than one figure are generally labeled with a same or similar number in all the figures in which they appear.

FIG. 1 illustrates an image of a negative impression with the front surface removed, in accordance with an exemplary embodiment of the invention;

FIG. 2 illustrates an image of a negative impression overlaid on an image of an area of a recipient jaw, including artifacts, in accordance with an exemplary embodiment of the invention;

FIG. 3 illustrates a computer representation of a negative impression overlaid on a computer representation of a recipient jaw area, in accordance with an exemplary embodiment of the invention;

FIG. 4 illustrates a computer representation of bore trajectories in an artifact-corrected computer representation of a negative impression and implant area, in accordance with an exemplary embodiment of the invention;

FIG. 5 illustrates a drilling template with bore trajectories, in accordance with an exemplary embodiment of the invention;

DETAILED DESCRIPTION OF EMBODIMENTS

An aspect of the present invention relates to producing an artifact-corrected image of a recipient jaw and its negative impression as a basis for creating a drilling template with properly aligned drill guides for drilling implant-receiving bores in a recipient jaw. To understand this process, reference will be made to a flow chart 1100 in FIG. 11, interspersed with references to FIGS. 1 through 4.

Figure 11:
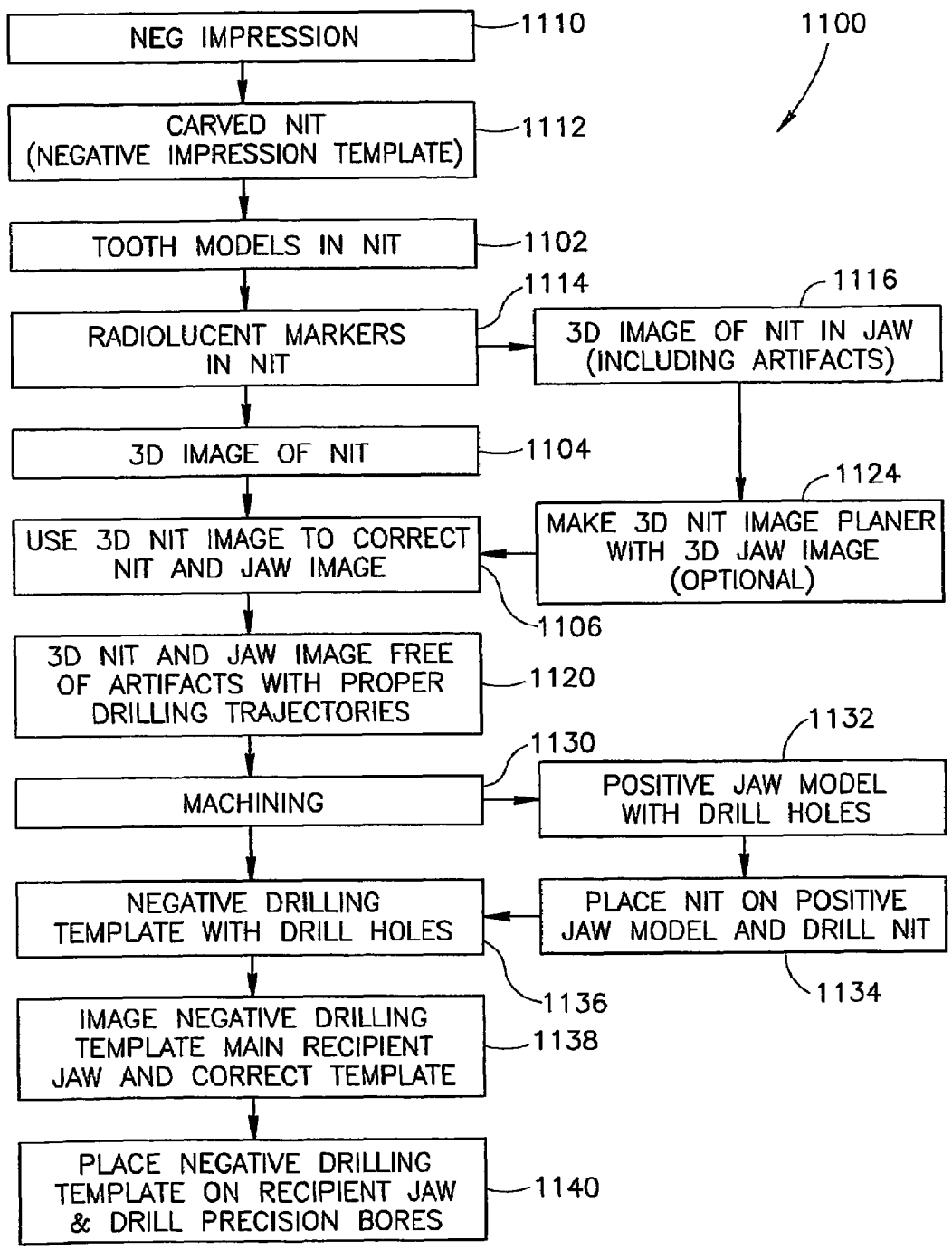
FIG. 11 illustrates a flow chart for forming a drilling template in the presence of metal inserts, in accordance with an exemplary embodiment of the invention.

In flow chart 1100 of FIG. 11, at 1110, a negative impression is made of the recipient jaw. Optionally, the negative impression at 1110 is prepared using a three-step mechanical impression method known in the art. First, a negative replica is taken directly from the patient teeth by conventional methods, for example using elastic viscose. The negative replica is filled with a hard material, for example gypsum (plaster) to form a replica of the implant area. A third (negative) impression is taken of the replica of the implant area. While a negative impression is made in three steps, it is optionally made in a single step or any other odd number of steps, as known in the art.

For the purposes of this application, a negative impression refers to the impression taken of the recipient jaw area. For the purposes of this application, a negative impression template, NIT, refers to a negative impression of the recipient jaw that has been revised in some way, for example so that it includes physical drill guides so that it is used as a drilling template within the recipient jaw.

Optionally, the negative impression is carved at 1112, forming a negative impression template, NIT, to adjust for complex curvatures that might prevent easy attachment and removal from the recipient jaw. Machinery that is used to form the negative impression template from the negative impression is, for example, standard dental machinery used for preparation and modification of prosthetic molds.

Optionally, models of one or more teeth to be implanted in the recipient jaw are placed in the NIT, at 1102. Using, for example, MRI, CT or another method, images are acquired of the NIT alone at 1104 and with the NIT placed in the recipient jaw at 1116. Optionally, prior to making these images, radiolucent markers are placed in the NIT at 1114 to ensure, for example, that the various images of the NIT will properly align with each other during image processing (at 1106).

FIG. 1 is a negative impression template image 114 of a lower jaw with depressions 110 and 124 of teeth in the lower jaw. Negative impression template image 114, for example, ends at a gum line 216. Image 100 is shown with a front surface removed to better visualize bores (for example bores 426 B, D and F in FIG. 4) that are, for example, placed within it.

In image 100, NIT image 114 contains tooth model images 112 that represent the upper portion of teeth that are to be implanted. The tooth models used to make the tooth model images 112 are, for example, of a different radiolucency than that of the negative impression template used to make NIT image 114 so they are easily identified in a CT or MRI image of NIT image 114. Optionally, to properly align two or more images of negative impression template image 114, radiolucent markers 116 are, for example, included in the NIT, for example, on either side of tooth impression 124 and at the side of tooth impression 110. These markers 116 have images that are distinguished from the NIT image 114 on a CT or MRI.

FIG. 2 illustrates a 3D digital image 200 of a negative impression template, placed in an image of the recipient jaw including existing images of teeth 210 and 211 and a jaw bone image 212 to which the prosthesis is to be connected. Negative impression template image 114 reveals the position of tooth implant images 112 and how they will fit over recipient jaw bone image 212. Artifacts 220, that distort the image, for example, appear in jaw bone image 212 due to a metal insert 266.

Optionally, a separation edge is made to allow a proper separation in image 200 between recipient jaw bone image 212 and negative impression template image 114, which is needed during further imaging steps. To define a separation edge, jaw bone image 212 is optionally defined by a plane encompassing radio opaque markers 116. As radio opaque markers 116 are independent of the complex boundary of jaw image 212, a separation edge based on markers 116 is easily recognized by edge detection image processing algorithms.

Additionally or alternatively, a shelf is created within the physical negative impression using modeling processing known to the art, for example, using standard impression modeling machinery. Optionally, this shelf is recognized by edge detection image processing algorithms, as separation plane 216, allowing proper separation in image 200 between jaw bone image 212 and negative impression template image 114. Additionally or alternatively, two radio opaque connecting line segments, along line 216 are added to the physical impression template that is used to make impression template image 114. Optionally, these connecting line segments, are similarly recognized as separation plane 216 by an edge detection image processing software. Additionally or alternatively, other methods are used that allow a separation plane 216, to be defined between negative impression template image 114 and jaw bone image 212. Optionally, no automatic, software-based methods are used to provide a separation line and the separation along separation plane 216 is made through manual inspection and manipulation of the computer representation.

Registration is a software process whereby the 3D digital image 100 of negative impression template image 114 alone, as seen in FIG. 1, is overlaid on a 3D digital image 200 so that their outlines match in spite of artifact distortion. Optionally, registration software processing utilizes, for example, at least one of the following methods: (a) lining up radiolucent markers in image 100 with those of image 200, (b) correlating the outline of image 100 with the outline of image 200, and (c) matching NIT features within image 100 and image 200. Additionally or alternatively, registration is accomplished manually by an operator who manipulates image 100 on image 200 using markers, the image outlines and/or matching features.

Artifacts 220, caused by an image of a metal insert 226 in tooth image 211, for example, appear as one or more star bursts 220 that distort image 200. Additionally or alternatively, artifacts appear as a spiral around metal insert image 226, causing distortion of image 200. Additionally or alternatively, artifacts appear in other forms that distort image 200. Such distortions, when left uncorrected, for example, utterly disrupt the boundary surfaces in image 200, leading to a misaligned drilling template.

During the registration process, any voxels that are above a plane defined by line 216 are corrected, for example, by voxel replacing software that replaces voxels in image 200 with voxels from image 100. This results in an artifact-corrected computer representation 300, seen in FIG. 3.

In FIG. 3, artifact distortions 220 that appeared in negative impression template image 114 above line 216 are no longer present. Portions of artifacts 220 that appeared below line 216 are present, but, for example, do not affect jaw bone image 212 in a manner that prevents proper manipulation of the computer representation in making a finished drilling template. Optionally, an operator is capable of manually manipulating computer representation 300, as necessary, in following subsequent steps necessary for malting a drilling template. Additionally or alternatively, image manipulation software manipulates computer representation so that it is appropriate for making a drilling template.

In flow chart of FIG. 11, the image of the NIT in the recipient jaw at 1116 contains artifacts, and is processed to optionally contain a planer edge at 1124. The NIT image at 1104 and the NIT and jaw image modified at 1124 are processed at 1106. Optionally, the NIT image made at 1104 is used to correct the artifacts present in the NIT and jaw image made at 1116.

FIG. 4 shows the formation of drilling template image 414 on jaw bone image 212 in a computer representation 400. Trajectories 420 A, C and E and their extensions 426 B, D and F, are manipulated in the computer representation on the basis of a variety of factors, for example, one or more of the following: (a) the position of embedded tooth models images 112, (b) the anatomy and structure of jaw bone image 212, (c) the position of tooth root images 316 which, unlike their upper sections that are missing, for example, aid in properly locating the bore drills in the computer representation.

In addition to trajectory position, the depth of lower extensions 426 B, D and F is optionally computed by image manipulation software so that the drilling does not extend deep enough to damage structures, for example nerve root 432.

Optionally, the depth of bores 420 is determined from recipient jaw bone image 212 anatomy, for example, thickness of bone stock, as seen in a CT, MRI or X-ray image. Additionally or alternatively, the trajectories of lower bores 426 is based upon the position and angle of tooth model images 112. Additionally or alternatively, the trajectories of lower bores 426 is based upon another process using a jaw model including structures, for example, nerve root 432 that will be explained below.

In FIG. 4, drilling template computer representation 400 is saved on information media or transmitted electronically, for example by electronic mail, to a modeling device, for example a Fast Prototyping machine. Optionally, the modeling device produces a drilling template 500, as shown in FIG. 5, with drilling guides 512 A, C and E, corresponding to bores 420 A, C and E in computer representation 400.

Referring to the flow chart in FIG. 11, at 1120, the computer representation of the NIT and jaw, which is corrected of artifacts, is modified to include drilling trajectories using one of the methods noted above. The resulting computer representation is sent to a modeling device, for example as a Fast Prototyping machine, at 1130. At 1130, different models are made, depending on the embodiment of the present invention used.

Figure 13:
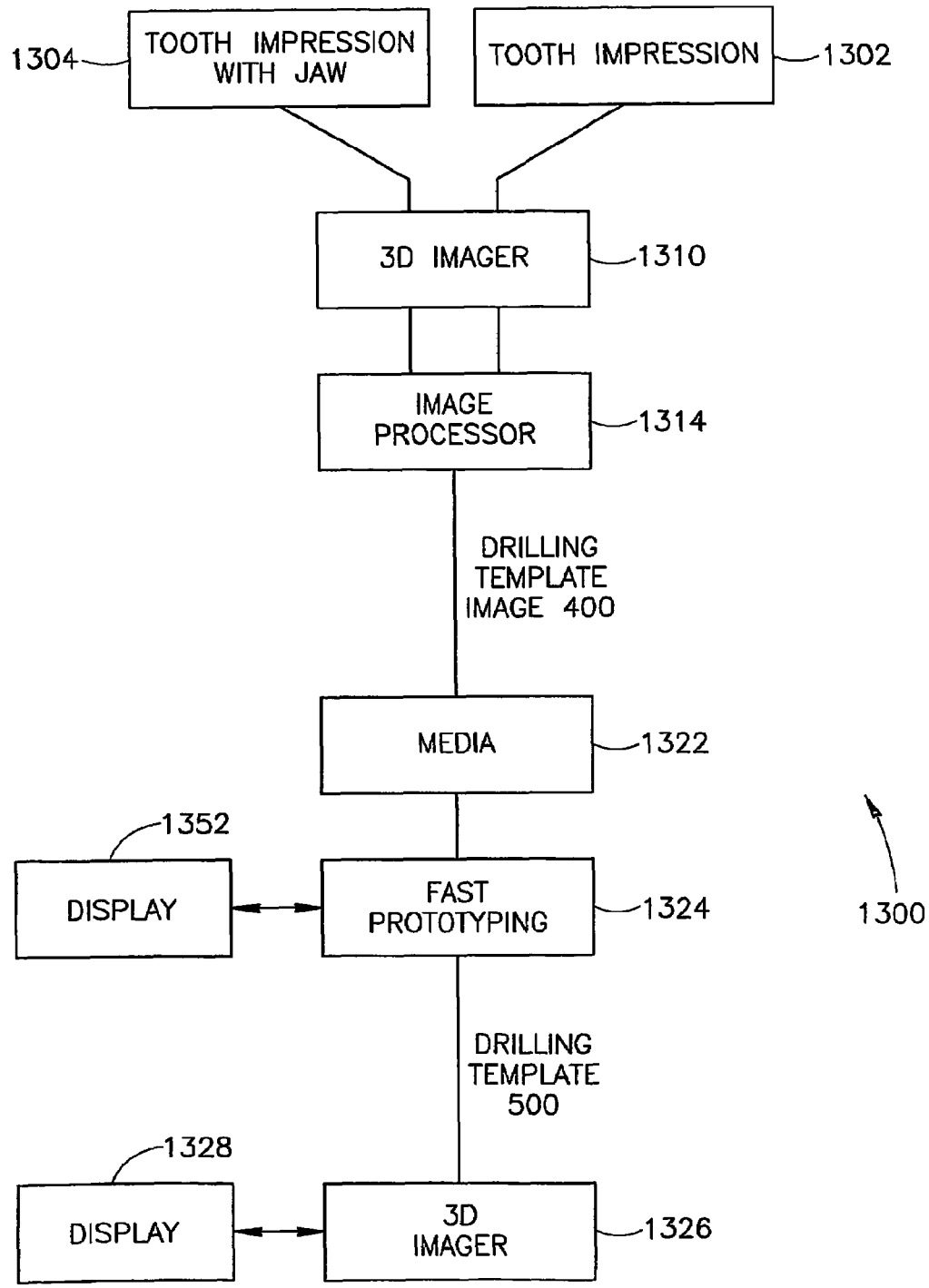
FIG. 13 is an exemplary setup of an apparatus to carry out the steps required in producing a drilling template, in accordance with an exemplary embodiment of the invention.

FIG. 13 provides a schematic illustration of a device 1300, suitable for producing the drilling template described above. A negative tooth impression is taken, optionally in a dental office, of a recipient jaw 1304 and modified to include mock replacement teeth. Optionally, it is sent to a 3D Imager 1310, which could be a CT, MRI or other 3D image provider, located, for example in the dental office. 3D Imager 1310 provides a 3D image of the jaw impression 1304 including, for example, an image separator such as an edge.

A tooth impression (negative impression) image 1302 is additionally made by 3D Imager 1310 and sent to Image processor 1314. Image processor provides Image Registration, using image registration software that recognizes the image separator on the two images, 1302 and 1304. Image processor 1314 is optionally located in the dental office. Additionally or alternatively, image processor 1314 is located at a distant site, for example a modeling laboratory.

Image Processor 1314 further provides a drilling template computer representation 400, including drilling trajectories, that is transferred to Media 1322. Media 1322 produces a digital computer representation that is optionally transferred to Fast Prototyping machine 1324 or similar modeling device, connected to a display 1352. Fast Prototyping machine 1324, for example, is located in a modeling area in the dental office. Additionally or alternatively, it is located in a modeling laboratory. Optionally, Fast Prototyping machine 1324 transforms Media 1322 into a drilling template 500.

Drilling template 500, for example, is transferred to an operator, for example a dentist, in a dental office, who places it on the recipient jaw for the purpose of determining that it seats properly. A 3D Imager 1326, for example a CT scanner or MRI, is used to produce a 3D image of the drilling template on the recipient jaw. The 3D image is then analyzed at Display 1328 by an operator, for example a dentist. Additionally or alternatively, the 3D image is analyzed and drilling template 500 is corrected using drilling template correction software, for example, in a modeling laboratory. Following correction, drilling template is used to drill bores in the recipient jaw.

According to an embodiment of the invention, modeling at 1130, for example by a Fast Prototyping machine, directly yields a negative drilling template at 1136 with properly aligned drilling guides for drilling bores in the recipient jaw. Optionally, this drilling template is created directly from the computer representation formed at 1120. At 1120, in addition to corrections for artifacts, the image is manipulated so that it contains proper drilling trajectories that are put in the drilling template.

Figure 10:
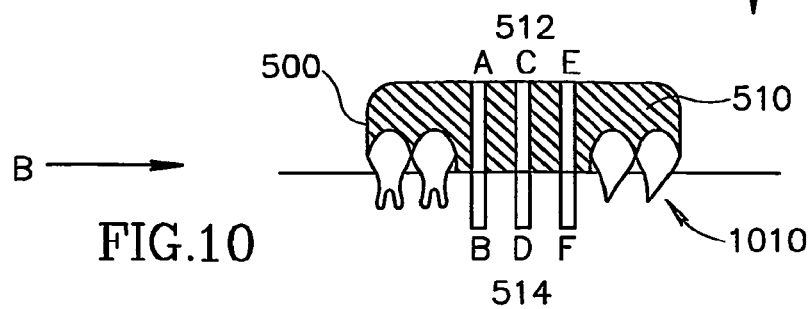
FIG. 10 illustrates a drilling template in place in a recipient jaw with bore trajectories drilled into the recipient jaw, in accordance with an exemplary embodiment of the invention.

As shown in FIG. 10, drilling template 500 is optionally placed on patient jaw 1010 to determine that it seats properly. When drilling template 500 does not seat properly over recipient jaw 1010, it will, for example, produce improperly lined-up bores 514 B, D, and F in recipient jaw 1010. In an embodiment of the present invention, in step 1140 of FIG. 11, prior to drilling the bores into the recipient jaw, additional or alternative methods are used to ensure that drilling template 500 of FIG. 10 properly seats in recipient jaw 1010.

Referring to FIG. 11, in one method for ensuring proper seating, the negative drilling template of step 1136 is placed in the recipient jaw and imaged in step 1138 using CT, MRI or other imaging methods. An improperly seated drilling template 500 within jaw 1010 will often have air pockets indicating that it is misaligned. Air pockets appear as high contrast areas between drilling template 500 and recipient jaw 1010. The anomalies are corrected in drilling template 500 until the high contrast areas in subsequent images disappear, indicating proper alignment.

An alternative embodiment of the present invention for establishing that the finished drilling template 500 will properly sit in the patient mouth utilizes a gypsum model of recipient jaw 912. Optionally, drilling template 500 is placed on gypsum model 912 and modified until it sits properly and drilling guides 512 A, C and E match trajectories 810 B, D and F. Upon satisfactory modification, drilling template 500 is placed in patient jaw 1010 and bores for the implants are drilled.

In an alternative embodiment, CT, MRI, US, X-ray or other medical imaging computer data are used as a basis for producing a plastic model including different internal tissues, for example bones, soft tissues, nerves, cartilage and etc. Each tissue is represented by a different material property, for example by varying color, impedance, toughness and etc.

Optionally, drilling template 500 is attached to this plastic model and the drilling guides, 512 A, C and E are assessed. Such assessment is, for example, accomplished by visualizing the color of the tissues in the plastic model in the path of the drill. When there is, for example, inadequate bone to securely attach the tooth implants, the position of the drilling guides 512 A, C and E are altered by an operator.

Additionally or alternatively, the impedance of the materials in the drill path is measured so that unless the impedance registers a certain level the operator is signaled by sounds given off by impedance detection software that the implants will not sit in the recipient jaw correctly, disrupting nerve conduction, for example. Drilling template 500 is then modified by an operator, for example in the dental office or in the laboratory, so that drilling guides, 512 A, C and E line up with appropriate tissue in jaw model 912.

Additionally or alternatively, an image is acquired of drilling template 500 on recipient jaw 1010 and the image is optionally processed by image overlay software to include the proposed implant bores superimposed on an image of drilling guides 512 A, C and E above and image of recipient jaw 1010. Optionally, if a discrepancy exists between the alignment of drilling guides, 512 A, C and E, and the proposed image of implant bores into jaw 1010, drilling template 510 is appropriately modified prior to proceeding. With this modification, bores to be made in the drilling template 510 match the calculated computer representations.

Once drilling template 500 is modified so that it sits correctly, implant bores 514 B, D and F are drilled into the recipient jaw. In Flow 1100, this is seen at 1140. Tooth implants are introduced into the drilled bores that align with adjacent teeth, giving an optimally aesthetically pleasing result.

Figure 8:
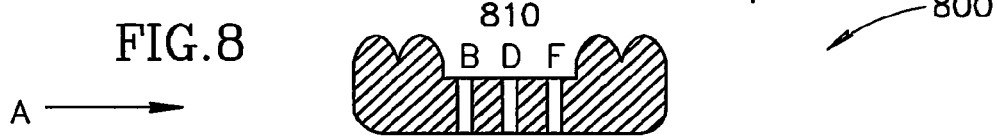
FIG. 8 illustrates a jaw model section with bore trajectories, in accordance with an exemplary embodiment of the invention.

In an embodiment of the present invention the digital modeling at 1130 produces only a model of the recipient jaw at 1132. Optionally, digital modeling at 1130 is not used to produce a negative template. Rather, the NIT made from the recipient jaw at 1110 in FIG. 11, is placed upon jaw model and at 1134, the drill holes in the jaw model are continued into the NIT, using a drill, to manually form a negative drilling template at 1136. This is shown in FIG. 8, wherein bores 810 B, D and F are made according to the trajectory of bores 426 B, D and F in computer representation 400.

Figure 9:
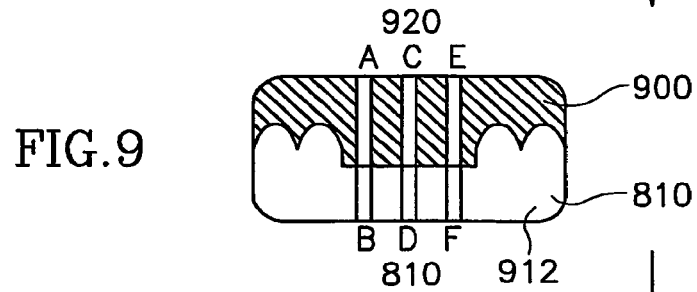
FIG. 9 illustrates bore trajectories in a section of a drilling template and a jaw model, in accordance with an exemplary embodiment of the invention.

FIG. 9 shows a drilling template 900 sitting upon jaw model 810. Drilling guides 810 B, D and F are continued from jaw model 810 into drilling template 900 to produce drilling guides 920, A, C and E. Optionally, drilling template 900 is then used as template 500 in FIG. 10 over jaw 1010 to drill implant-receiving bores in jaw 1010.

Figure 12:
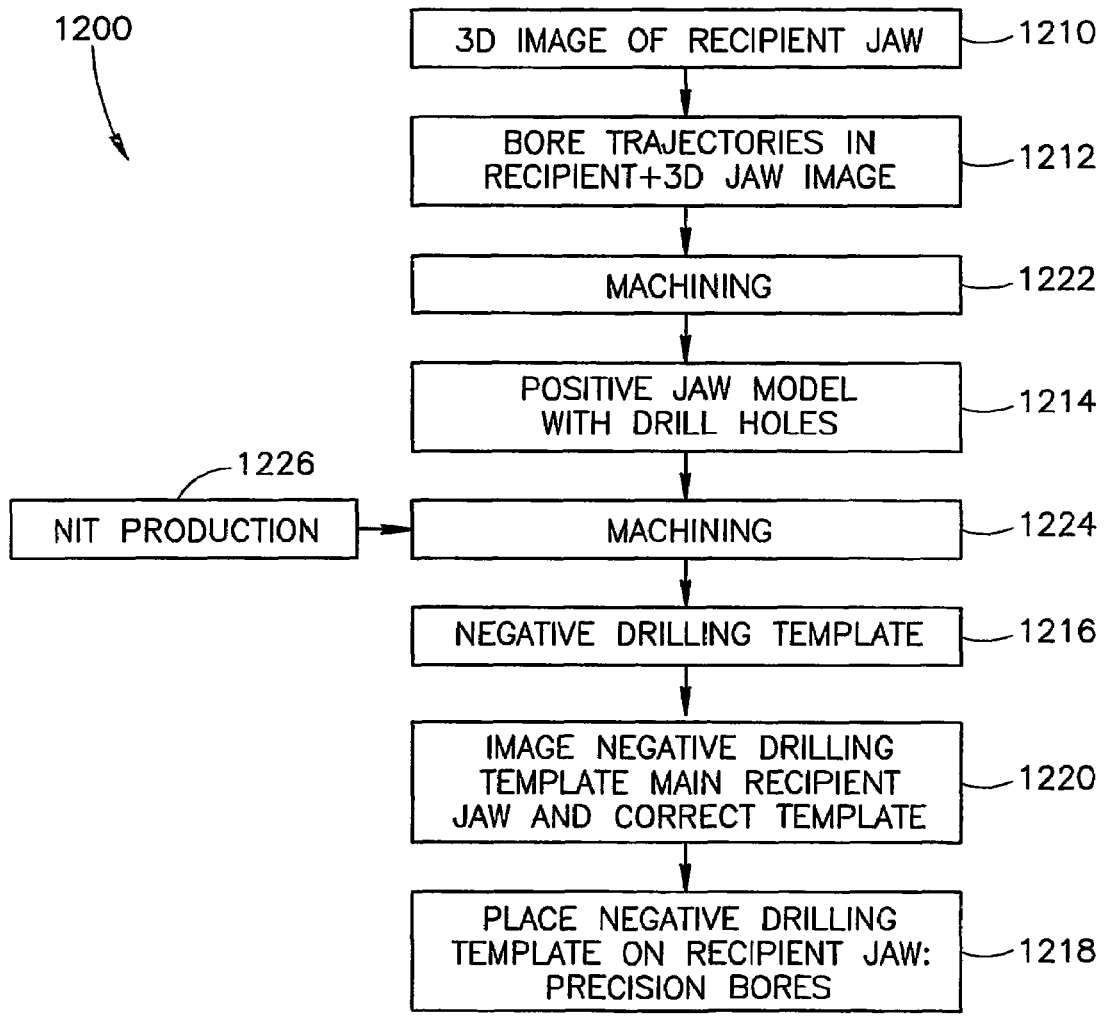
FIG. 12 illustrates a flow chart for forming a drilling template in the absence of metal inserts, in accordance with an exemplary embodiment of the invention.

In an aspect of an embodiment of the present invention, a drilling template is created from an image of a jaw that is free of metal inserts that cause artifacts as seen flow chart 1200 in FIG. 12. At 1210, an image of the recipient jaw area is taken, for example, using CT, MRI or any other imaging technique. At 1212, bore trajectories are added to form a computer representation of the jaw. Optionally, this computer representation is electronically transferred to a modeling operation at 1222, for example a Past Prototyping machine.

Optionally, the modeling operation digitally creates a model of the recipient jaw with one or more drill hole guides 1214. This model is sent with a Negative Impression template, produced at 1226, to a modeling operation 1224 that drills through the drill hole guides in the recipient jaw model into the negative impression template, producing a negative drilling template complete with drill guide holes at 1216.

Additionally or alternatively, a jaw model produced at modeling operation 1222 is returned to the dentist who places a negative impression template of the recipient jaw on the jaw model. Optionally, the dentist drills through the drill hole guides in the recipient jaw model into the negative impression template, producing a negative drilling template with drill guides.

Figure 6:
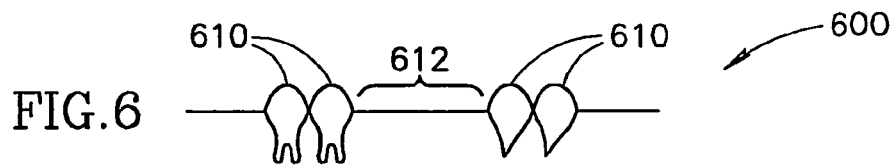
FIG. 6 illustrates a computer representation of a CT scan of an implant area, in accordance with an exemplary embodiment of the invention.
Figure 7:
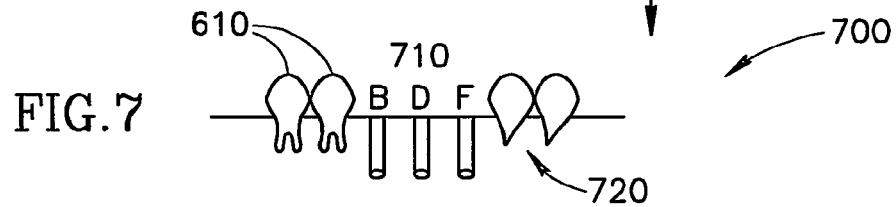
FIG. 7 illustrates planned bore trajectories in a computer representation of an implant area, in accordance with an exemplary embodiment of the invention.

Referring to FIG. 6, a scan as indicated at 1210, is made to create lower jaw image 600 that includes teeth images 610 and implant image area 612. FIG. 7 illustrates bore trajectories 710 B, D that have been added to a computer representation 700 of an implant area. Optionally, when there are complexities in the jaw curvature, the surface representation of teeth images 610 in computer representation 700 are modified to allow easy attachment or removal of a negative impression template from the recipient jaw area 1010. Optionally, such modification is made by an operator, for example, in a dental office. Computer representation 700 is saved on information media, or entered into an electronic delivery system, for example electronic mail, and sent to a modeling device, for example located in the dental office or, for example, at a distant site, for example a modeling laboratory.

The resultant model 800 is processed to form model 900 and patient jaw 1010 is drilled as described above. Referring to the Flow Chart of FIG. 12, at 1220, drilling template is placed on the recipient jaw and modified as noted above. At 1218, the negative drilling template is used to drill bores for receiving implants in the recipient jaw.

Referring back to FIG. 13, one can appreciate that many prior art apparati may be suitable for use in the present invention, if appropriately modified. For example, Image Processor 1314, may utilize one of many prior art imaging systems, provided that they are appropriately adapted to provide proper image merging, reduction of artifacts and/or production of a merged image. Alternatively or additionally the present invention may include a dedicated imager and work station unit in combination for producing a drilling template, said image and work station being located in a single location and/or in a single encasement.

In an exemplary embodiment, system 1300 comprises a negative jaw impression adjuster adapted for adjusting said impression to allow easy manipulation of said impression on said recipient jaw. Optionally, system 1300 comprises a tooth implant model setter adapted to set one or more tooth implant models in said negative jaw impression, prior to producing said images. In an exemplary embodiment of the present invention, the impression adjuster and/or the tooth implant setter receive data directly from the imager. Alternatively or additionally, an operator inputs data into system 1300 that to produce an appropriately modified negative impression.

In an exemplary embodiment, system 1300 includes a reference marking recorder adapted to place one or more markings in said negative jaw impression. Alternatively or additionally, system 1300 comprises a drilling template modeler that models drilling template 500 based upon said reproduced image.

In an exemplary embodiment, Image Processor 1314 includes a dedicated processing unit with appropriate hardware, and optionally dedicated software. Alternatively or additionally, Image Processor 1314 includes a general CPU capable of executing appropriate activities based upon software modules that are stored in memory. For example, Image Processor 1314 comprises one or more of the following software modules:

a) an image merging software module that merges first and second digital images to form a reproduced image having reduced artifacts with reference to said first image;

b) a voxel alignment module that, when voxel images are provided, aligns the voxels of said first digital image with the voxels of said second digital image;

c) a voxel substituting module that substitutes at least a portion of said voxels of said first digital image for voxels of said second digital image;

d) an image conglomerator software module that conglomerates a portion of the first image with a portion of the second image, wherein the images are non-inclusive. Optionally, the conglomerator conglomerates the upper portion of the first image and the lower portion of the second image; and e) a drill trajectory imposer module that imposes one or more drilling trajectories in said artifact-reduced image.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents, which perform the same function, even if the structure or acts are different, as known in the art. Therefore, the scope of the invention is limited only by the elements and limitations as used in the claims.

The invention claimed is:

1. A method for producing an artifact-corrected image of a negative jaw impression of a jaw of a patient, the jaw containing teeth, the artifacts resulting from the presence of existing metal in at least one of the patient's teeth or jaw, comprising:

forming a negative impression of said patient's jaw;

producing a first digital image of said negative impression of said patient's jaw;

producing a second digital image of said negative impression of said patient's jaw and said patient's jaw, including said artifacts; and comparing said first digital image and said second digital image to produce an artifact-corrected computer representation of said negative impression and said patient's jaw.

2. The method of claim 1, further comprising adjusting said negative jaw impression during formation to allow easy manipulation of said impression on said patient's jaw.

3. The method of claim 1, further comprising setting at least one tooth implant model in said negative impression of said patient's jaw, prior to producing said images.

4. The method of claim 1, further comprising incorporating at least one reference marking in said negative impression of said patient's jaw, wherein said at least one reference marking is visible in said first and second images.

5. The method of claim 1, wherein said first and second digital images comprise voxels.

6. The method of claim 1, further comprising forming an image comprised of an upper portion of the first image and a lower portion of the second image wherein said upper portion is free of said artifacts.

7. The method according of claim 1, further comprising setting at least one drilling trajectory in said artifact-corrected computer representation.

8. The method of claim 1, further comprising using said artifact-corrected computer representation to produce a drilling template.

9. The method of claim 1, further comprising using said artifact-corrected computer representation to produce a model of said patient's jaw.

10. The method of claim 9, further comprising using said model of said patient's jaw to produce a drilling template.

11. The method of claim 1, further comprising using said negative impression of said patient's jaw to produce said drilling template.

* * * * *